United States Patent

Nakamura et al.

[11] Patent Number: 6,007,804
[45] Date of Patent: Dec. 28, 1999

[54] IL-6 AS SERUM URIC ACID DECREASING COMPOUND

[75] Inventors: Toru Nakamura, Kyoto; Takanori Ueda, Fukui-ken; Hiroshi Tsutani, Fukui-ken; Shinji Kishi, Fukui-ken; Nobuyuki Yoshio, Fukui-ken, all of Japan

[73] Assignee: Applied Research Systems ARS Holding N.V.

[21] Appl. No.: 09/027,618

[22] Filed: Feb. 23, 1998

[30] Foreign Application Priority Data

Mar. 13, 1997 [JP] Japan ........................................ 9-58759

[51] Int. Cl.[6] .......................... A61K 38/20; A61K 38/00
[52] U.S. Cl. .............................. 424/85.2; 930/141; 514/2; 530/351
[58] Field of Search ........................... 424/85.2; 930/141; 514/2

[56] References Cited

PUBLICATIONS

Yoshio et al. Purin, Pirimijin Taisha, 21(1), 48–49, Jan. 1997.
Brozik et al. J Rheumatol 19 (1), 63–68, Jan. 1992.

Weber, J. et al., Phase I Trial of Subcutaneous Interleukin–6 in Patients with Advanced Malignancies, J. Clin. Oncology, 11(3), Mar. 1993, pp. 499–506.

Hirano, T., et al., Purification To Homogeneity and Characterization of Human B–cell Differentiation Factor (BCDF or BSFp–2), Proc. Nat. Acad. Sci. USA, 82, Aug. 1985, pp. 5490–5495.

Kishimoto, T., The Biology of Interleukin–6, Blood, 74(1), Jul. 1989, pp. 1–10.

*Primary Examiner*—Cecilia J. Tsang
*Assistant Examiner*—Michael Borin
*Attorney, Agent, or Firm*—Pillsbury Madison & Sutro LLP

[57] ABSTRACT

The present invention provides a serum uric acid decreasing agent which contains interleukin-6 (IL-6) as the active ingredient together with a pharmaceutically acceptable carrier; and a method for decreasing the serum uric acid level which comprises administering interleukin-6 (IL-6) in an effective amount to a patient.

6 Claims, 1 Drawing Sheet

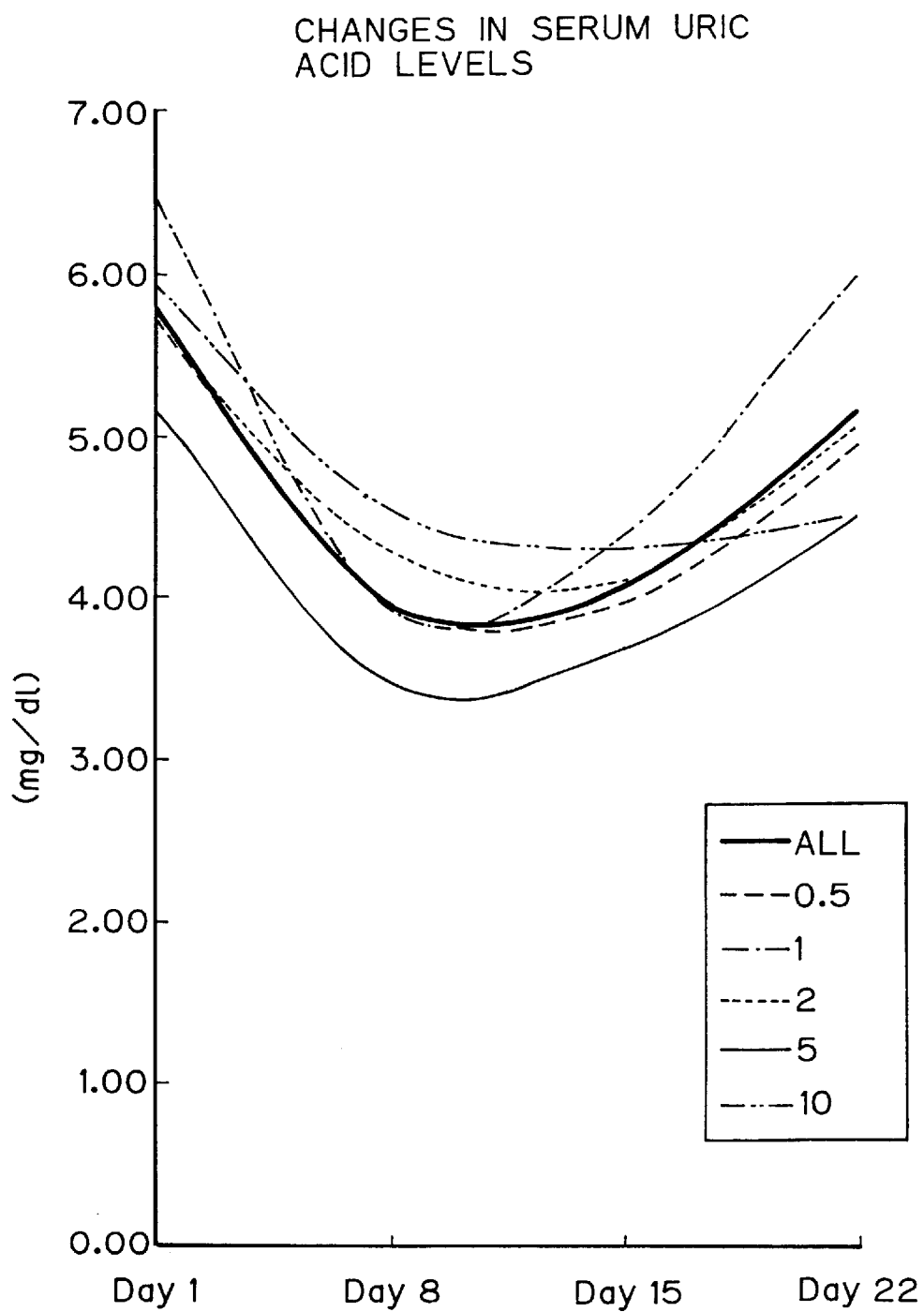

IL-6 AS SERUM URIC ACID DECREASING COMPOUND

BACKGROUND OF THE INVENTION

This invention relates to a serum uric acid decreasing agent and a method for decreasing serum uric acid levels.

With changes in diet, gout has come to be regarded as a serious adult disease. It is known that the acute and intractable pain of gout is caused when uric acid excessively accumulates in the body and is deposited as calcium urate in the fingers and toes. Known methods for treating gout involve: 1) use of uric acid synthesis inhibitors to inhibit the accumulation of uric acid in the body; and 2) use of uric acid excretion promoters to accelerate the rapid excretion of uric acid accumulated in the body.

There is only one uric acid synthesis inhibitor (i.e., allopurinol) readily available today. On the other hand, probenecid, sulfinpyrazone and benzbromarone are known as uric acid excretion promoters. However, it is known that allopurinol should be employed with caution, since it induces some problems such as systemic hypersensitivity. Similarly, uric acid excretion promoters such as benzbromarone may produce an attack of gout, when used inappropriately.

On the other hand, interleukin-6 (IL-6), which is classified as an inflammatory cytokines, is a molecule which has various biological activities, for example, it can cause fever or headache and induce the formation of acute phase proteins such as CRP and fibrinogen in the liver [Hibi, M. et al., Interleukin-6, Meneki Yakuri (Immunological Pharmacology) 7(4):103, 1989; Taai, H. et al., IL-6 Sansei Saibo to sono Seiri Kassei no Tayosei (IL-6 Producing Cells and Multiplicity in their Physiological Activities), Rinsho Meneki (Clinical Immunology) 21(8):1225, 1989; Weber J., et al.: Phase I trial of subcutaneous interleukin-6 in patients with advanced malignancies, J. Clin. Oncology 11(3):499, 1993]. IL-6 also has an effect of increasing blood platelets and thus various clinical tests are now under way to make use of this effect.

SUMMARY OF THE INVENTION

The present invention provides a serum uric acid decreasing agent of a novel type different from synthetic drugs. The present invention further aims at providing a novel method of treating gout, in particular, preventing and alleviating a gout attack.

BRIEF DESCRIPTION OF THE DRAWING

FIG. 1 is a graph showing changes in the serum uric acid level in association with the administration of r-hIL-6.

DETAILED DESCRIPTION OF THE INVENTION

During clinical tests aimed at the application of IL-6 to the treatment of cancer, the present inventors found that this cytokine induces a decrease in the serum uric acid level. The mechanism of the decrease in the serum uric acid level by IL-6 may be explained by the fact that the excretion of uric acid from the liver is accelerated. Therefore, the present invention provides a serum uric acid decreasing agent containing IL-6 as the active ingredient together with a pharmaceutically acceptable carrier.

During an attack of gout, the uric acid metabolic homeostasis becomes abnormal. Accordingly, the discovery that IL-6 decreases the serum uric acid level opens up the possibility that symptoms of a gout attack can be prevented or relieved by using this cytokine. It is known that IL-6 in the serum increases during a gout attack, and hence, it was assumed that IL-6 might serve as an inflammatory mediator. However, the fact that "IL-6 decreases serum uric acid levels", was not known before.

IL-6, which is the active ingredient of the drug of the present invention, falls within the category of cytokines inherently produced by organisms in vivo. Therefore, it does not cause any problem in terms of safety. Although it is preferable to use IL-6 of human origin, it is expected that IL-6 originating in other animals will exert the effects of the present invention similar to human IL-6. Thus, the present invention includes in its scope use of such non-human source IL-6 as the active ingredient.

IL-6 may be purified from natural sources or it may be purified from the medium of cultured cells, for example, fibroblasts [Hirano, T., Taga, T., Nakano, N., Yasukawa, K., Kashiwamura, S., Shimizu, K., Nakajima, K., Pyun, K. H. & Kishimoto, T.: Purification to homogeneity and characterization of human B cell differentiation factor (BCDF or BSFp-2), Proc. Nat. Acad. Sci. USA 82: 5490–5494 (1985)]. Recent technical advancements have made it possible to produce a recombinant IL-6 on a large scale by sing gene manipulation techniques. It is also preferable to use a recombinant IL-6. Regarding methods for producing and purifying a recombinant IL-6, refer to Kishimoto, T.: The Biology of Interleukin-6, BLOOD 74 (1): 1–10 (1989), JP (Kokai) Hei 1-503354 and JP (Kokai) Hei 2-186996. Moreover, commercial IL-6 products are available from Ajinomoto Co., Ltd., Ares-Serno NV and Sandoz Ltd. In the field of genetic engineering, it is widely known that IL-6 can be modified by deleting, substituting or inserting a part of the amino acids thereof without substantially altering its inherent biological activities. Accordingly, the active ingredient of the present invention may be such a modified IL-6.

IL-6 is administered to an adult in need of a decrease in serum uric acid at a dose of from 0.1 to 100 $\mu$g/kg, on the basis of the pure protein, preferably from 0.5 to 10.0 $\mu$g/kg, one to several times per day. However, the said dose is indicated merely as a typical range. Namely, a doctor should determine the dose in practice depending on the age, body weight, sex, disease conditions, etc. of individual patients. It is generally necessary to decrease the serum uric acid level, when an attack of gout arises or a risk of an attack is predicted such as at a time immediately before, during or after eating or drinking. When the serum uric acid level exceeds 8 mg/dl, it is also necessary to take some measures to lower the level.

IL-6 may be administered to a patient either orally or parenterally. The term "parenteral administration" includes intravenous administration, intramuscular administration, subcutaneous administration, nasal administration by aerosols, etc.

In the case of oral administration, IL-6 may be formulated into tablets, powders, granules, troches or capsules together with appropriate solid carriers, for example, lactose, kaolin, sucrose, talc, gelatin, agar, pectin, acacia and magnesium stearate. When IL-6 is orally administered in the form of syrups or soft gelatin capsules, use may be made of syrups, vegetable oils or water as liquid carriers.

In the case of parenteral administration, IL-6 may be processed into sterile aqueous solutions or suspensions for injection or sterile powders from which sterile solutions or suspensions for injection can be prepared before using. These parenteral preparations should be sterile and have such a fluidity as to allow easy injection. From this viewpoint, it is possible to use, as the liquid medium, a solvent or dispersant such as water, ethanol, polyols (glycerol, propylene glycol, liquid polyethylene glycol, etc.), or appropriate mixtures thereof as well as vegetable oils. To achieve an appropriate fluidity, use may be made of surfactants, if needed. To prevent the contamination with microorganisms, it is also possible to add paraben, chlorobutanol, phenol, sorbic acid, thimerosal, etc. to the preparation. It is preferable that the preparation further contains an isotonic agent such as sugar and sodium chloride and a buffer agent capable of giving a pH value compatible with the pH value in vivo. The injections may further contain an absorption retarding agent such as aluminum monostearate and gelatin to regulate the absorption of IL-6.

Sterile injections can be prepared by mixing IL-6 in the required amount with ingredients as cited above in an appropriate solvent followed by sterilization by filtration. Injections to be dissolved before using can be prepared by a sterile filtration of a solution containing IL-6 together with desired ingredients and pipetting the solutions into vials or ampules followed by vacuum-drying or freeze-drying.

The serum uric acid decreasing agent of the present invention is useful for preventing and/or treating not only gout but also vulgar psoriasis, hemolytic anemia, nephropathy and chronic leukemia. In these cases, the serum uric acid decreasing agent may be administered in almost the same manner (dose, timing, frequency, etc.) as for treating gout.

EXAMPLES

Example 1

From 48 hours after the completion of chemotherapy, 0.5 to 10.0 μg/kg/day of a recombinant human interleukin-6 (r-hIL-6) (Sigosix) was subcutaneously administered to patients with solid cancer once a day continuously for 3 to 14 days. During this period, the serum uric acid level was measured at intervals of 1 week. As a result, all of the patients except in one case showed decreases in their serum uric acid levels. That is to say, the average serum uric acid levels of the all cases on the days 1, 8, 15 and 22 were respectively 5.77, 3.96, 4.07 and 5.51 mg/dl. This serum uric acid decreasing effect quickly disappeared after the completion of the administration of r-hIL-6. On individual basis, the maximum decrease was 5.4 mg/dl while the average decrease was 2.09 mg/dl. In this Example, the observed effect was not dependent on the dose over the dose range employed. Thus, it is assumed that this effect is independent of dose within a certain range of administration dose. The minimum serum uric acid levels were observed in the middle of the administration period in many cases and thus a clear relationship between the administration period and the serum uric acid decreasing effect is yet to be determined. The results are shown in Table 1 and FIG. 1. In FIG. 1, "ALL" means the average of the all cases (20), while "0.5", "1", "2", "5" and "10" show respectively the average of the test groups with the corresponding doses.

TABLE 1

| No. | Dose (μg/kg/d) | Administration period | Day 1 | Day 8 | Day 15 | Day 22 | Amount of decrease |
|---|---|---|---|---|---|---|---|
| 1 | 0.5 | 14 days | 5 | 3.9 | 4.5 | 4.6 | 1.1 |
| 2 | 0.5 | 14 | 5.4 | 4 | 3.3 | 4.4 | 2.1 |
| 3 | 0.5 | 14 | 6.7 |  | 4.1 | 5.8 | 2.6 |
| 4 | 1 | 14 | 7.4 | 3.8 | 4 | 8 | 3.6 |
| 5 | 1 | 10 | 5.6 | 3.5 | 6 | 6.1 | 2.1 |
| 6 | 1 | 14 | 7.6 | 3.9 | 3.2 | 4.6 | 4.4 |
| 7 | 1 | 14 | 4.5 | 2.7 | 3.1 | 4.1 | 1.8 |
| 8 | 1 | 14 | 7.2 | 5.7 | 5.6 | 7.2 | 1.6 |
| 9 | 2 | 14 | 6.2 | 4.4 | 5.1 | 7.2 | 1.8 |
| 10 | 2 | 14 | 5.4 | 5.4 | 4.6 | 3.6 | 1.8 |
| 11 | 2 | 10 | 3.9 | 4.2 |  |  | −0.3 |
| 12 | 2 | 13 | 8.4 | 3.6 | 3.1 | 5 | 5.3 |
| 13 | 2 | 11 | 4.4 | 3.8 | 3.6 | 4.4 | 0.8 |
| 14 | 5 | 3 | 3.9 | 3 | 2.9 | 2.9 | 1 |
| 15 | 5 | 7 | 7.4 | 3 | 4.8 | 5.2 | 4.4 |
| 16 | 5 | 14 | 4 | 3.4 | 3.2 | 4.2 | 0.8 |
| 17 | 5 | 4 | 5.2 | 4.7 |  |  | 0.5 |
| 18 | 5 | 14 | 5.3 | 3.2 | 3.8 | 5.7 | 2.1 |
| 19 | 10 | 6 | 6.3 | 5.9 | 4.3 | 4.5 | 2 |
| 20 | 10 | 7 | 5.5 | 3.2 |  |  | 2.3 |
| Average |  |  | 5.77 | 3.96 | 4.07 | 5.15 | 2.09 |

Example 2

From 48 hours after the completion of chemotherapy, 2.0 μg/kg/day of r-hIL-6 was subcutaneously administered to a patient with malignant blood cancer once a day continuously for 5 days. During this period, the serum uric acid level and the uric acid in urine were observed everyday. As a result, the excretion of uric acid was accelerated while the serum uric acid level was decreased from the day 1 of the administration. After the termination of the administration of the drug, the uric acid in urine and the serum uric acid level each quickly returned to the level prior to the administration of r-hIL-6.

Based on these results, it is concluded that r-hIL-6 has an effect of decreasing serum uric acid.

What is claimed is:

1. A method for decreasing the serum uric acid level of a patient who is in need of a decrease in the serum uric acid level which comprises administering IL-6 in an amount effective to decrease the serum uric acid level.

2. The method as claimed in claim 1, wherein said patient in need of a decrease in the serum uric acid level is one suffering from gout.

3. The method as claimed in claim 1 or 2, wherein said IL-6 is human IL-6.

4. The method as claimed in claim 1, wherein said IL-6 is recombinant IL-6.

5. The method as claimed in claim 1 or 2, wherein IL-6 is administered to an adult in a dose of from 0.5 to 10.0 μg/kg body weight, on the basis of the pure protein, one to several times per day.

6. The method as claimed in claim 5, wherein the administration is performed orally or by injection.

* * * * *